United States Patent
Loosme

(10) Patent No.: US 7,630,848 B2
(45) Date of Patent: Dec. 8, 2009

(54) ANALYSIS SYSTEM AND METHOD IMPLEMENTING DISTRIBUTED PROCESSING

(75) Inventor: Raivo Loosme, Viken (SE)

(73) Assignee: Foss Analytical A/B, Hoganas (SE)

(*) Notice: Subject to any disclaimer, the term of this patent is extended or adjusted under 35 U.S.C. 154(b) by 487 days.

(21) Appl. No.: 11/168,993

(22) Filed: Jun. 29, 2005

(65) Prior Publication Data

US 2006/0271319 A1 Nov. 30, 2006

(30) Foreign Application Priority Data

May 25, 2005 (SE) .................................. 0501194

(51) Int. Cl.
*G06F 19/00* (2006.01)
*G06F 17/40* (2006.01)

(52) U.S. Cl. ........................ 702/85; 73/1.01; 73/1.02; 73/23.2; 73/23.21; 702/30; 702/32

(58) Field of Classification Search ............... 702/85, 702/28, 32, 1, 22, 23, 24, 25, 26, 27, 30, 702/31, 86, 87, 88, 104, 127, 187, 188, 189; 703/12, 6; 73/1.01, 1.02, 1.03, 19.01, 19.02, 73/23.2, 23.21, 23.22, 23.23, 23.35, 23.36, 73/23.37, 53.01, 61.41, 61.43, 61.48, 61.52, 73/61.57, 61.71, 866; 340/500, 501, 540, 340/870.01, 870.04, 870.07, 870.16
See application file for complete search history.

(56) References Cited

U.S. PATENT DOCUMENTS

| | | | |
|---|---|---|---|
| 5,517,427 A | 5/1996 | Joyce | |
| 6,560,546 B1* | 5/2003 | Shenk et al. | 702/30 |
| 6,751,576 B2* | 6/2004 | Hall et al. | 702/183 |
| 6,944,486 B2* | 9/2005 | Braig et al. | 600/310 |
| 6,958,479 B2* | 10/2005 | Burling-Claridge et al. | 250/339.09 |
| 7,194,369 B2* | 3/2007 | Lundstedt et al. | 702/104 |
| 2001/0037182 A1* | 11/2001 | Hall et al. | 702/104 |
| 2002/0095419 A1 | 7/2002 | Parce | |
| 2002/0178789 A1 | 12/2002 | Sunshine et al. | |
| 2003/0122080 A1 | 7/2003 | Burling-Claridge et al. | |
| 2003/0154044 A1* | 8/2003 | Lundstedt et al. | 702/104 |
| 2007/0143037 A1* | 6/2007 | Lundstedt et al. | 702/30 |

FOREIGN PATENT DOCUMENTS

WO    WO 0169403    9/2001

OTHER PUBLICATIONS

International Search Report May 25, 2005.

* cited by examiner

*Primary Examiner*—Edward R Cosimano
(74) *Attorney, Agent, or Firm*—Harness, Dickey & Pierce, P.L.C.

(57) ABSTRACT

A distributed analysis system may include at least one analysis instrument for generating sample data from a sample at a local site. A storage device may hold a library of calibration models at a site remote from the local site). A data processor, which may be integral with or separate from the analysis instrument, may determine a trait of the sample using a calibration model selected from the library and the sample data. The data processor may be located at the local site and may be connectable to the storage device via a telecommunications link. The data processor may temporarily retain the selected calibration model received via the telecommunications link.

10 Claims, 2 Drawing Sheets

ANALYSIS SYSTEM AND METHOD IMPLEMENTING DISTRIBUTED PROCESSING

PRIORITY STATEMENT

This US non-provisional application claims benefit of priority under 35 USC §119 from Swedish Patent Application No. 0501194-5, filed on May 25, 2005, the entire contents of which are incorporated herein by reference.

BACKGROUND

1. Field of the Invention

The present invention relates generally to a distributed analysis system and to a method that may be implemented for analyzing materials employing the system. More particularly, the system and method may relate to the optical analysis of materials to determine characteristics thereof.

2. Description of the Related Art

Analysis instruments, such as optical (e.g., Near Infra Red (NIR)) spectrophotometers, may be employed in a variety of industries to analyze various material samples to make a quantitative and/or a qualitative determination of various characteristics thereof, such as concentrations of constituents of the material and/or physical properties, for example. In agricultural and food industries, for example, the oil, protein and moisture content of grain and other crops; the fat content of meat; the fat, protein, lactose and urea content of milk; the quality of grain and of wine and other vinicultural products; may be determined using NIR analysis. It is also known to apply similar NIR analysis in the medical, pharmaceutical, chemical and petro-chemical industries.

An optical analysis of samples may be considered as an "indirect" determination because the optical measurements may be an indirect indication of the characteristic being determined. Results may be obtained in a matter of minutes (for example) in contrast to the conventional "direct", sometimes chemical, analysis methods which may take hours or days (for example) to perform and which may be carried out at central laboratories that may be remote from the site where the sample was taken.

Since the optical analysis is an indirect determination, a link may be established between the optical measurement and the characteristic and/or property of interest (hereinafter referred to as "trait"). As is known in the art, the trait may be represented in an equation summing products of weighting coefficients and values from the derivative of the optical absorbance and/or transmission spectrum that may be acquired by the analysis instrument. A first order derivative of an absorbance spectrum may be used but higher order derivatives may also or alternatively be used. The undifferentiated absorbance (or in some cases transmission) spectrum and any or all derivatives thereof will be referred to jointly and/or severally as the context demands, as a "sample spectrum" or more generally as "sample data".

To measure the desired trait of an unknown sample, spectra may be collected from a multiplicity of known sample materials similar to the unknown sample. The trait(s), be it a physical characteristic and/or a constituent concentration, to be determined may be known in the known samples. Using the collected sample spectra obtained from the known samples and from the knowledge of the associated trait, the weighting coefficients of the equations relating the known trait to the collected spectra may be determined by (for example) multiple regression, by partial least squares regression and/or by other statistical techniques including those employing artificial neural nets. The process of determining the values of the weighting coefficients may be known as "calibration". After the calibration coefficients have been determined, the unknown sample may be analysed using the analysis instrument (and/or an instrument intended to be substantially identical in performance so that the same calibration coefficients may be applied) together with the calibration coefficient that have been derived from the known sample materials. Instead of measuring the spectral response at selected specific wavelengths, which may be known and/or may be presumed to correlate with the trait, the sample spectra may be collected at wavelengths distributed throughout the spectral region appropriate to the trait (e.g., the NIR spectral region) and coefficients and equations relating the trait to spectral measurements throughout that spectral region may be developed.

Calibration coefficients may be derived for each trait to be determined and for each type of sample material. Calibration coefficients may be collected in "calibration libraries" for access and use by a data processor which may be programmed to carry out the determination of the desired trait. Calibration libraries may additionally or alternatively include the complete calibration equations, including the calibration coefficients, for use by the data processor. The term "calibration model" may refer either jointly or severally to the calibration coefficients and the calibration equations associated with a particular trait, as demanded by the context in which it is employed herein. It will be understood that similar methodology may be applied to other types of sample data that may be generated using other indirect measurement modalities employed by other types of analysis instrument.

An analysis system which employs an NIR spectrophotometer is known from for example, U.S. Pat. No. 6,751,576 to Hall et al. and from US 2003/0122080 to Burling-Claridge et al. (the contents of both of which are incorporated herein by reference in their entirety). In both disclosures, the data processor may be located at a site that is remote of the analysis instrument and a communication link may be provided to permit data transfer between the analysis instrument and the data processor.

This known centralized analysis system may include a storage device that may be located at a site remote of the analysis instrument. For example, the storage device may be collocated with the data processor. The storage device may retain a calibration library for access by and use in the data processor. The data processor may select an appropriate calibration model from the library in dependence on data received from a particular remote analysis instrument over the communications link. The data processor may then apply the selected model to sample data which may be provided over the communications link. Using the same communications link, the trait determined as a result of the application of the selected calibration model may be provided to the local site, for example to an output device in the vicinity of the analysis instrument that generated the sample data. In this manner, the library of calibration models may be maintained centrally which may facilitate calibration model upgrading, for example as new known samples are added and/or as statistical analysis methodology is developed. Moreover, development of a calibration library may be costly and time consuming, and therefore maintaining the library centrally and remote from the user of an analysis instrument may provide greater control over the access to and use of the calibration models in the library.

Although conventional systems and methods are generally thought to provide acceptable performance, they are not without shortcomings. For example, sample data such as an optical spectrum, even if compressed, may represent a relatively large amount of data that may be transmitted over the communications link. Accordingly, measures may be taken to ensure that the communications link remains stable over the time period required to transmit the data and to ensure that the transmitted data is accurately represented at the central processor. Furthermore, the analysis results to be transmitted over the often publicly accessible communications link (e.g., a telecommunications link) may be sensitive information which, if misappropriated, may be used to the commercial disadvantage of the intended recipient.

SUMMARY

According to an example, non-limiting embodiment of the present invention, a distributed analysis system may include at least one analysis instrument for generating sample data from a sample at a local site. A storage device may be provided at a site that is remote from the local site. The storage device may hold a library of calibration models. A data processor may determine a trait of the sample using a calibration model selected from the library and the sample data. The data processor may be located at the local site. The data processor may be connectable to the storage device via a telecommunications link. The data processor may temporarily retain the selected calibration model received via the telecommunications link.

According to another example, non-limiting embodiment of the present invention, a method of analyzing a material sample at a local site may involve generating sample data at the local site. A calibration model may be selected from a library of calibration models held at a site remote of the local site. The selected calibration model may be employed in a data processor to determine a desired trait of the material sample using the generated sample data. The determination of the desired trait may be performed at the local site. The selected calibration model may be transmitted via a telecommunications link from the remote site to be retained temporarily at the local site for access by the data processor.

BRIEF DESCRIPTION OF THE DRAWINGS

Example, non-limiting embodiments of the present invention will become apparent from a consideration of the following description with reference to the accompanying drawings.

DETAILED DESCRIPTION OF EXAMPLE, NON-LIMITING EMBODIMENTS

Figure 1:
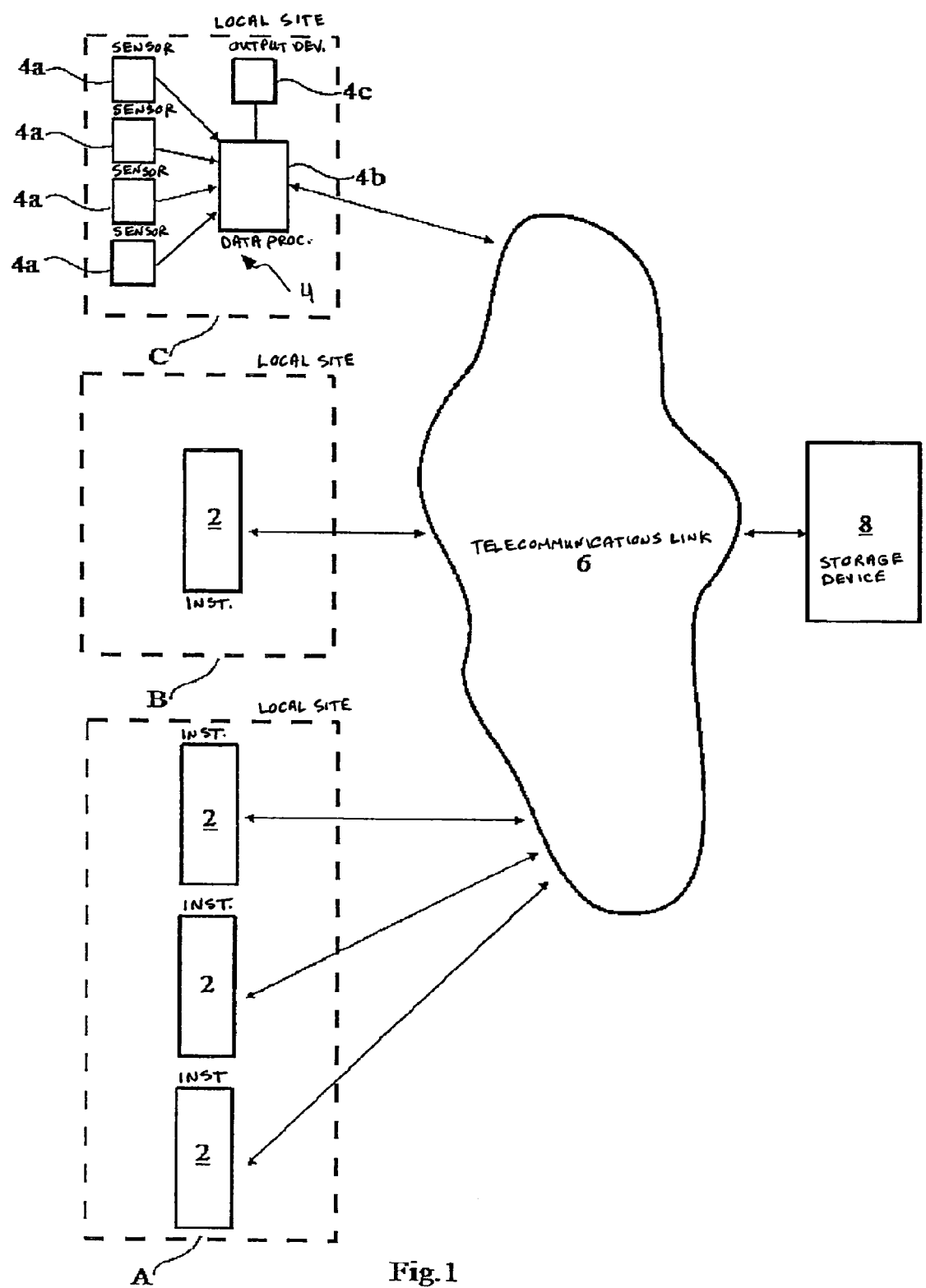
FIG. 1 is a schematic representation of an analysis system according to an example, non-limiting embodiment of the present invention.

With reference to FIG. 1, the analysis system may include spectrographic instruments 2, 4 that may be provided at a plurality of separated local sites A, B, C, which may be any geographical locations in the world having access to a telecommunications link 6. By way of example only, the spectrographic instruments 2, 4 may be NIR spectrographic instruments and the telecommunications link 6 may be the internet. In alternative embodiments, the telecommunications link 6 may be (for example) conventional telephone lines and/or wireless transceivers that may be capable of transmitting data between geographically separated sites.

In order to exemplify, at least partially, the versatility of the analysis system, site A may have a plurality (e.g. 3) of individual instruments 2. Each instrument 2 may be separately connectable to the telecommunications link 6. Site B may have only a single instrument 2, which may be identical to those of site A. And site C may have an instrument 4 that may include a network of a plurality of separate sensor units 4a. The sensor units 4a may generate sample data and may be connected to a data processor 4b. The data processor 4b may be connected to an output device 4c such as a display and/or a printer, for example. The data processor 4b may be connected to the telecommunications link 6. It will be appreciated that the instruments 2, 4 may be configured in a variety of different way to provide the functionality described herein and still remain within the scope of the invention as claimed. For example, the data processor 4b may include a server at the local site C. The server may be connected to a central data processor in the vicinity of the sensors 4a and/or the output device 4b.

A storage device 8 may be provided as part of the analysis system. The storage device 8 may be located at a site that is geographically removed from the local sites A, B, C. The storage device 8 may be configured for bi-directional communication with the analysis instruments 2, 4 across the telecommunications link 6. In this example embodiment, the storage device 8 may be a computer that may be used to store and manipulate a calibration library. The storage device 8 may include multiple computers, perhaps performing different functions (as discussed below) such as a communications function, a library update function and/or a calibration model selection function. In practice, such a combination may be configured to behave as a single entity.

Figure 2:
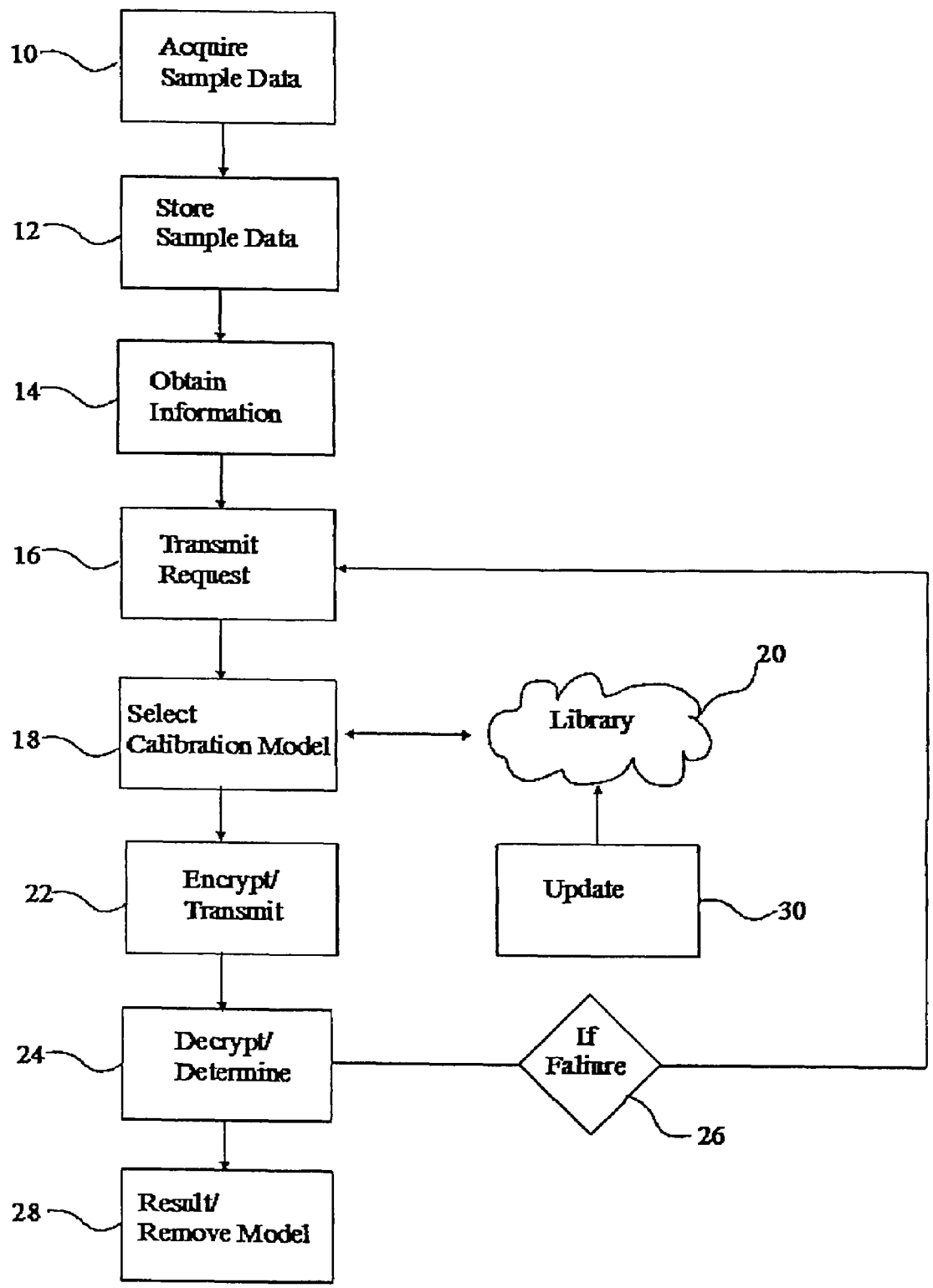
FIG. 2 is a flow chart of a method according to an example, non-limiting embodiment of the present invention.

FIG. 2 illustrates an example method of analyzing sample materials to determine a trait thereof by using the system illustrated in FIG. 1. It will be appreciated that the various processes of the method need not be performed in the sequence illustrated but rather the method is only generally illustrative of the processes to be undertaken.

At process 10, the separate sensor units 4a and/or those integral with the analysis instrument 2 may acquire sample data to be used in determining the trait. In the present embodiment the instruments 2, 4 may be NIR spectrographic instruments so that the sample data may be a sample spectrum, recorded in a conventional manner. This sample data, at process 12, may be passed to the data processor 4b or that data processor (not shown) integral within the analysis instrument 2 where it may be stored, either permanently or temporarily.

In this example embodiment, an information gathering process 14 may be performed. It will be apparent from what is disclosed below that the information gathering process 14 may, in some embodiments, be omitted, for example where only one analysis instrument is employed to determine only one trait and/or a fixed, known set of traits.

The information may be gathered either automatically and/ or entered manually by a user. The gathered information may identify the type of material being analyzed and the individual instrument performing the analysis. By way of example only, in the further discussion of the method of FIG. 2, it will be assumed that each instrument 2 and sensor 4a may have an associated unique identifier, such as a Globally Unique Identifier (GUID) and/or a barcode identifier (for example), that may be automatically read and provided as an electronic signal and that information concerning the sample being analyzed may be entered manually by a user using a user interface such (for example) as a touch screen, a keyboard, a pointing device or any combination thereof. This user input sample information may for example indicate the particular variety of grain being analyzed and the trait or traits to be determined.

In the present example the unique identifiers and the user input information may be transmitted, in a process 16, via the telecommunications link 6 to the storage device 8 at a remote site.

In the example embodiment, the storage device 8 may retain a calibration library 20. The storage device 8 may also retain a database that may index the identities of the analysis instruments 2, 4 and the individual sensors 4a of the analysis instrument 4, which may be obtained by the storage device 8 from the electronic identifiers transmitted to the storage device 8, with a group or groups of calibration models (including for example a group comprising the entire library 20) from within the library 20 that may be made available to the so identified analysis instrument. In a process 18, a calibration model or models, if available from the indexed group, may be selected in dependence of the user input, for example at least one identifying trait to be determined. An encrypted representation of this selected calibration model or models may be transmitted, in the process 22, to the relevant data processor at the appropriate site A, B, C. The appropriate site and data processor may be identified from the instrument ID in the associated indexed database.

As a further example of the versatility of the example analysis system, as illustrated in FIG. 1, the storage device 8 may be configured to hold as a portion of the library 20 a plurality of calibration models, each usable in the determination of the same trait but which is constructed, in a known manner as described above, using different collections of known samples. Thus, for example, site A and site B may be each populated with essentially the same analysis instrument 2 to perform essentially a determination of the same trait. However, each site A, B may be owned by a different entity and the analysis instruments 2 may be considered as belonging to independent networks at site A and at site B. The owner of site A may provide additional known samples to augment or replace those used in the generation of a generally accessible group within the calibration library 20 and so have created a specific group of calibration models within the library 20. The owner of site A may wish access to this specific group to be restricted to only those instruments that are indexed as belonging to site A, whilst the owner of site B may access the same storage device 8 but have made available only calibration models that are indexed as belonging to the generally accessible group.

The owner of site C may operates (for example) a processing plant converting grain to flour and may have sensors 4a located at different parts of the local site C to monitor the process in real time. In this example, the data processor 4b may receive electronic identifiers that identify each of the sensors 4a individually and may have an electronic identifier to identify the site B. It is this site identifier which may be transmitted at 16 to the storage device 8. The library 20 of the present embodiment may include calibration models which may be solely accessible to site C that may be employed in the determination of traits of the grain and traits of intermediate process materials as well as the quality of the end product, here milled flour (for example). It is envisaged that in a further version of this embodiment, site C may be provided with an automated process control system that may be co-operably linked to the analysis system. It will be appreciated that the process control system may be configured to provide instructions to the data processor 4b that may cause a particular one of the sensors 4a to generate sample data. The data processor 4b may be configured to provide the determined traits to the process control system for use in (for example) monitoring and/or varying the operation of the processing plant.

It will be appreciated that the storage device 8 may be readily provided with appropriate computer coding and indexed database such that an operator (independent of the owners of the local sites A, B, C, for example) of the storage device 8 may provide a service that satisfies the requirement of all the different owners.

On receipt via the telecommunications link 6 of the encrypted transmission according to the process illustrated at 22, the data processor, at a process 24, may attempt to decrypt the received encrypted model. If decryption fails, for example because of a corrupted transmission, a transmission break and/or the erroneous receipt of a calibration model not intended for the site, then at process 26 the information may be re-transmitted to the storage device 8 via the telecommunications link 6 according to process 16 and the processes 18-22 may be repeated.

According to process 24, once the received encrypted calibration models are successfully decrypted, they may be temporarily retained in the data processor which may be caused to execute appropriate determination software to perform, in a generally known manner, a determination of the desired trait or traits from the sample data which was acquired at process 10 and stored at process 12.

For example, the data processor 4b, for example, of the analysis instruments 2,4 may be provided with a permanent data storage such as a hard disk (for example) and a temporary data storage such as an addressable volatile memory (for example). Here the terms permanent and temporary may be interpreted relative to one another in the context of the invention. The data processor may be programmed to store the acquired sample data in the permanent memory and to hold the decrypted calibration model in the temporary memory. The determination software may cause the data processor to retrieve the acquired sample data, here in the form of a sample spectrum in to a working memory and to access the calibration model.

Once the determination of the trait or traits is completed, at process 28 the results may be provided to a user, such as by displaying the results at an output (for example) which may be integral with (not shown) the analysis instrument 2 and/or a separate component 4c of the instrument 4. The results may also be retained in the permanent memory.

At process 28 of the example embodiment, the data processor may determine whether the received calibration model is to be removed from access by the data processor by erasing it from the addressable volatile memory.

It is envisaged that the data processor may be adapted to remove the calibration model dependent on other predetermined conditions being met. Thus for example, the data processor may be configured with a counter which may be an elapsed time counter or a usage counter, counting the number of times a determination has been performed according to process 24, and adapted to remove the model at the earliest of reaching a predetermined count or when a software initiated "shutdown" may be performed to end an analysis session.

It is also envisaged that an update of the contents of the storage device 8, process 30, may be included in a method according to an example embodiment of the present invention. This updating may, as illustrated, involve a modification of the calibration library 20 whereby the calibration models may be updated and/or new models added to expand the trait determination capabilities of the analysis system and/or may involve a replacement of the entire library. New users may be added to the indexed database and/or the access rights of existing users to the calibration models may be varied.

The above and other features of the invention including various and novel details of construction and combination of parts have been described with reference to the accompanying drawings and pointed out in the claims. It will be understood that the particular method and system embodying the invention has been shown by way of illustration only and not as a limitation of the invention. The principles and features of this invention may be employed in varied and numerous embodiments without departing from the scope of the invention.

What is claimed is:

1. A distributed analysis system comprising:
   at least one analysis instrument for generating sample data from a sample at a local site;
   a storage device at a site remote from the local site, the storage device holding a library of calibration models; and
   a data processor to determine a trait of the sample using a calibration model associated with the trait selected from the library held in the storage device and the sample data, the data processor being located at the local site and being connectable to the storage device via a telecommunications link, the data processor being adapted to temporarily retain the selected calibration model received via the telecommunications link.

2. The distributed analysis system as claimed in claim 1, wherein the data processor is configured to transmit data to the storage device via the telecommunications link usable to select the calibration model.

3. The distributed analysis system as claimed in claim 1, wherein the data processor temporarily retains the selected calibration model in an addressable volatile memory and removes the selected calibration model therefrom dependent on a predetermined condition being fulfilled.

4. A method of analyzing a material sample at a local site comprising:
   generating sample data at the local site;
   selecting a calibration model from a library of calibration models held at a site remote of the local site; and
   employing the selected calibration model in a data processor to determine a desired trait of the material sample using the generated sample data, the determination of the desired trait being performed at the local site and the selected calibration model associated with the desired trait being transmitted via a telecommunications link from the remote site to be retained temporarily at the local site for access by the data processor.

5. The method as claimed in claim 4, wherein the method further comprises transmitting data from the local site via the telecommunications link, the data being usable at the remote site in the selection of the calibration model from the library of calibration models.

6. The method as claimed in claim 4, further comprising removing the selected calibration model from access by the data processor upon fulfillment of a predetermined condition, selected to make access to the model by the data processor temporary.

7. The method as claimed in claim 6, wherein the predetermined condition is the completion of a single determination of a desired trait.

8. A distributed analysis system comprising:
   at least one analysis instrument for generating sample data from a sample at a local site;
   a storage device at a site remote from the local site, the storage device holding a library of calibration models; and
   a data processor to determine a trait of the sample using a calibration model associated with the trait selected from the library held by the storage device and the sample data, the data processor being located at the local site and being connectable to the storage device via a telecommunications link, the data processor to temporarily retain the selected calibration model received via the telecommunications link,
   wherein the data processor is configured to transmit data to the storage device via the telecommunications link usable to select the calibration model.

9. A method of analyzing a material sample at a local site comprising:
   generating sample data at the local site;
   selecting a calibration model from a library of calibration models held at a site remote of the local site;
   employing the selected calibration model in a data processor to determine a desired trait of the material sample using the generated sample data, the determination of the desired trait being performed at the local site and the selected calibration model associated with the desired trait being transmitted via a telecommunications link from the remote site to be retained temporarily at the local site for access by the data processor; and
   transmitting data from the local site via the telecommunications link, the data being usable at the remote site in the selection of the calibration model from the library of calibration models.

10. A distributed analysis system comprising:
    a plurality of analysis instruments located at a plurality of local sites, each analysis instrument for generating sample data from a sample;
    a storage device at a site remove from the local sites, the storage device holding a library of calibration models; and
    a plurality of data processors located at the local sites, each of the analysis instruments operably connected to a different one of the plurality of data processors, each of the data processors to determine a trait of the sample using a calibration model associated with the trait selected from the library held by the storage device and the sample data, each data processor being connectable to the storage device via a telecommunications link.

* * * * *